US011213221B2

(12) United States Patent
Thomas et al.

(10) Patent No.: US 11,213,221 B2
(45) Date of Patent: Jan. 4, 2022

(54) METHOD AND APPARATUS FOR ANALYZING PULMONARY PERFORMANCE

(71) Applicant: KoKo IT, LLC, Longmont, CO (US)

(72) Inventors: Norman Thomas, Golden, CO (US); Edmond Chu, Erie, PA (US)

(73) Assignee: KoKo IT, LLC, Longmont, CO (US)

( * ) Notice: Subject to any disclaimer, the term of this patent is extended or adjusted under 35 U.S.C. 154(b) by 138 days.

(21) Appl. No.: 14/254,591

(22) Filed: Apr. 16, 2014

(65) Prior Publication Data
US 2014/0228700 A1 Aug. 14, 2014

Related U.S. Application Data

(62) Division of application No. 11/431,905, filed on May 10, 2006, now Pat. No. 8,721,561.

(60) Provisional application No. 60/679,782, filed on May 10, 2005.

(51) Int. Cl.
*A61B 5/087* (2006.01)
*A61B 5/08* (2006.01)
*A61B 5/091* (2006.01)
*A61B 5/097* (2006.01)
*A61B 5/00* (2006.01)

(52) U.S. Cl.
CPC ......... *A61B 5/0875* (2013.01); *A61B 5/0813* (2013.01); *A61B 5/091* (2013.01); *A61B 5/097* (2013.01); *A61B 5/7225* (2013.01); *A61B 5/7264* (2013.01)

(58) Field of Classification Search
None
See application file for complete search history.

(56) References Cited

U.S. PATENT DOCUMENTS

| 2,853,873 | A | | 9/1958 | Hollobaugh |
| 3,172,406 | A | * | 3/1965 | Bird ................. A61M 11/06 128/200.18 |
| 4,083,367 | A | | 4/1978 | Porner et al. |
| 4,256,100 | A | | 3/1981 | Levy et al. |
| 4,520,812 | A | | 6/1985 | Freitag et al. |
| 4,573,462 | A | | 3/1986 | Baum |
| 4,660,547 | A | * | 4/1987 | Kremer, Jr. ............ A61B 5/411 128/200.18 |
| 4,680,956 | A | | 7/1987 | Huszczuk |

(Continued)

FOREIGN PATENT DOCUMENTS

| CN | 1324256 | 11/2001 |
| CN | 106214152 | 12/2016 |

(Continued)

OTHER PUBLICATIONS

Miller et al., Standardisation of spirometry, 2005, European Respiratory Journal, vol. 26 No. 2, pp. 319-338). (Year: 2005).*

(Continued)

*Primary Examiner* — Michael R Bloch
(74) *Attorney, Agent, or Firm* — Sheridan Ross P.C.

(57) ABSTRACT

A method for pulmonary testing includes, while a patient inspires through the testing device, injecting a test gas at a selected flowrate toward an open end of the testing device. The method also includes measuring a flow rate of the inspired gas, which comprises the test gas. The method further includes measuring a concentration of a selected test gas component in the inspired gas.

18 Claims, 4 Drawing Sheets

(56) References Cited

U.S. PATENT DOCUMENTS

| | | | |
|---|---|---|---|
| 4,850,371 A * | 7/1989 | Broadhurst | A61B 5/0205 128/207.14 |
| 4,926,852 A * | 5/1990 | Zoltan | A61M 15/0086 128/200.23 |
| 5,022,406 A | 6/1991 | Tomlinson | |
| 5,036,847 A | 8/1991 | Boussignac et al. | |
| 5,193,551 A | 3/1993 | Pilipski | |
| 5,256,918 A | 10/1993 | Suzuki | |
| 5,297,543 A * | 3/1994 | Larson | A61M 15/0086 128/200.14 |
| 5,540,233 A | 7/1996 | Larsson et al. | |
| 5,558,085 A * | 9/1996 | Rubsamen | A61M 15/0045 128/200.14 |
| 5,598,836 A * | 2/1997 | Larson | A61M 15/0086 128/200.14 |
| 5,752,506 A | 5/1998 | Richardson | |
| 5,778,874 A * | 7/1998 | Maguire | A61M 16/0051 128/204.22 |
| 6,026,809 A * | 2/2000 | Abrams | A61M 15/0028 128/200.22 |
| 6,139,506 A * | 10/2000 | Heinonen | A61B 5/091 600/529 |
| 6,192,876 B1 * | 2/2001 | Denyer | A61B 5/087 128/204.18 |
| 6,306,099 B1 | 10/2001 | Morris | |
| 6,415,642 B1 | 7/2002 | Crapo et al. | |
| 6,584,971 B1 * | 7/2003 | Denyer | A61M 15/00 128/203.12 |
| 7,114,367 B1 | 10/2006 | Owens | |
| 7,201,166 B2 | 4/2007 | Blaise et al. | |
| 7,431,031 B2 | 10/2008 | Hete et al. | |
| 8,721,561 B2 | 5/2014 | Thomas et al. | |
| 9,186,090 B2 | 11/2015 | Chu et al. | |
| 10,206,608 B2 | 2/2019 | Higgins et al. | |
| 2005/0172966 A1 * | 8/2005 | Blaise | A61M 16/12 128/204.21 |
| 2006/0258949 A1 | 11/2006 | Thomas et al. | |
| 2009/0038371 A1 | 2/2009 | Verbraak et al. | |
| 2019/0175066 A1 | 6/2019 | Higgins et al. | |

FOREIGN PATENT DOCUMENTS

| | | |
|---|---|---|
| DE | 4127599 A1 | 2/1993 |
| DE | 100 38 818 A1 | 2/2002 |
| EP | 1109018 | 6/2001 |
| JP | 06-121785 | 5/1994 |
| JP | 07-155379 | 6/1995 |
| JP | 09-051950 | 2/1997 |
| JP | 2002-136595 | 5/2002 |
| WO | WO 06/122231 | 11/2006 |

OTHER PUBLICATIONS

Ferraris Respiratory, Eagle Comprehensive Pulmonary Laboratory, downloaded from http://www.groupferraris.com/ferrarisresporatory/usa/products/pdfs/Eagle.pdf, 2 pages, 2005.
Office Action for Canadian Application No. 2,608,242 dated Jul. 30, 2013, 3 pages.
Office Action for Canadian Application No. 2,608,242 dated Jun. 11, 2014, 2 pages.
Office Action for Canadian Application No. 2,608,242 dated Aug. 25, 2015, 3 pages.
Office Action for Canadian Application No. 2,608,242 dated Aug. 25, 2016, 2 pages.
Office Action for Chinese Application No. 200680015992.9, dated Jul. 12, 2010, 13 pages.
Office Action for Chinese Application No. 200680015992.9, dated Jun. 16, 2011, 7 pages.
European Search Report for European Application No. 06770214.2, dated Feb. 2, 2012, 6 pages.
Office Action for European Application No. 06770214.2, dated Jan. 3, 2013, 3 pages.
Office Action for European Application No. 06770214.2, dated Oct. 17, 2013, 4 pages.
Office Action for Japanese Application No. 2008-511350, dated Nov. 1, 2011, 7 pages includes English translation.
Office Action for Japanese Application No. 2008-511350, dated Apr. 25, 2012, 5 pages includes English translation.
International Search Report and Written Opinion for PCT/US06/18206, dated May 1, 2008, 9 pages.
Office Action for Chinese Application No. 201210113457.4, dated Nov. 26, 2013, 15 pages.
Graham et al., "2017 ERS/ATS standards for single-breath carbon monoxide uptake in the lung," *Eur Respir J* 2017; 49:1600016 (https://doi.org/10.1183/13993003.00016-2016), 31 pages.
Jensen et al., "Quality control of DL, CO instruments in global clinical trials," *European Respiratory Journal* 33(4):828-834, 2009.
Miller et al., "Series ATS/ERS Task Force: Standardisation of Lung Function Testing, General considerations for lung function testing, Edited by V. Brusasco, R. Crapo and G. Viegi No. 1 in this Series," *Eur Respir J* 26:153-161, 2005.
Wanger et al., "Series ATS/ERS Task Force: Standardisation of Lung Function Testing," Edited by V. Brusasco, R. Crapo and G. Viegi, No. 3 in this Series Standardisation of the measurement of lung volumes, Eur Respir J 26:511-522, 2005.

* cited by examiner

METHOD AND APPARATUS FOR ANALYZING PULMONARY PERFORMANCE

This U.S. patent application is a divisional of co-pending U.S. patent application Ser. No. 11/431,905 filed May 10, 2006, which claims the benefit of U.S. Provisional Application No. 60/679,782, filed May 10, 2005, the entire disclosure of which is hereby incorporated herein by reference.

FIELD OF THE INVENTION

The invention relates generally to pulmonary function testing and particularly to a device and method for measuring pulmonary functions in real-time or near real-time using controlled sample gas injection into the gas delivery system.

BACKGROUND

It is becoming increasingly important for healthcare providers to determine accurately pulmonary functions and mechanics in patients due to the prevalence of pulmonary diseases such as chronic bronchitis and emphysema. Many of the tests for pulmonary functions and mechanics use the techniques of gas dilution. In these tests, the patient inspires a gas mixture of known composition, typically stored in pressurized gas tanks or cylinders supplied by gas manufacturers. Inside the patient's lungs, some of these gas components become diluted by the gas within the lungs prior to the inhalation and/or by diffusion of the gas components through the alveoli. Pulmonary function and lung mechanics information can be derived by measuring and analyzing the composition and volume of the gas the patient exhales. Trace gases in the inspired gas mixtures include carbon monoxide and acetylene (each of which is used to measure gas diffusion across the alveoli) and helium and methane (each of which is used to measure the dead space in the lung cavity and/or pulmonary testing device). As will be appreciated, carbon monoxide and acetylene absorb readily and rapidly into the bloodstream while helium and methane do not. In this case, the volumes of the carbon monoxide or acetylene component and the helium or methane in the inspired and/or expired gas are determined and used along with the known composition of the sample gas, to calculate the volume of carbon monoxide or acetylene absorbed by the lungs. Carbon dioxide concentration in the expired gas can also be measured to ascertain lung diffusion because the concentration of carbon dioxide is directly related to the amount of oxygen absorbed into the bloodstream.

A typical pulmonary testing device (e.g., Eagle™ from Ferraris Respiratory, Inc.) is shown in FIG. 1. The device 100 includes a breathing conduit 104 that includes a patient mouthpiece 108, first and second outlets 112 and 116 for the discharge of exhaled air and intake of ambient inhaled air, respectively, and a test gas intake assembly 120. Balloon valves 124 and 128 open and close respectively the outlets 112 and 116. The test gas intake assembly 120 comprises a diaphragm 132 biased by a spring 136 and connected to a closure arm 140 that opens and closes the test gas introduction port 144 of conduit 148 upon demand (referred to as a demand valve). When the patient closes the balloons 124 and 128 and inhales, the diaphragm 132 is drawn downwards and the closure arm 140 repositioned as shown by the dotted lines. In this position, the port 144 is opened, thereby introducing pressurized test gas of known composition into the device 100 via conduit 148. The test gas is subsequently inhaled by the patient via the patient mouthpiece 108.

The patient can exhale immediately or after a determined time, depending on the type of test being conducted. A series of gas component sensors denoted by block 152 measure the concentrations of various selected gas components in the inspired and/or expired gas stream(s). Additionally, a gas flow measuring device 156 measures the flow rate of the inspired and/or expired gas stream, as desired.

The volume of a gas component actually inspired by the patient is given by the following equation:

$$V_X = (V_F \times F_X) - [(F_X - F_A) \times V_{DS}]$$

where $V_F$ is the total gas volume actually inspired by the patient, $F_X$ is the fraction of the selected gas component in the tank volume, $F_A$ is the concentration of the selected gas component in the ambient atmosphere (or in the device 100 before the test), and $V_{DS}$ is the interior volume of device 100 (dead space volume).

If the gas component has negligible diffusion rate through the alveoli into the blood stream, exhaled gas concentration measurements will allow estimations of the lung volume at the start of inhalation. Using gas such as carbon monoxide that has a high diffusivity through the alveoli, exhaled gas concentration measurements will provide an estimate of the lung diffusion properties.

This device 100 can have disadvantages. For example, it can be complex, expensive, physically large and unwieldy, and difficult to use. It typically may not be used for a number of pulmonary tests, such as pulmonary tests conducted while the patient is exercising.

The pre-mixed gases used in pulmonary function and lung mechanics testing can also be costly. The logistics associated with the ordering, storing, and disposal of the specialized gas cylinders also add to the complexity of the operation of a pulmonary function laboratory.

SUMMARY

These and other needs are addressed by the various embodiments and configurations of the present invention. The present invention can measure a variety of lung functions and mechanics using a breathing device in which the test gas is introduced without the use of demand valves. Due to the use of rapid gas analyzers, the accuracy of the measurements does not depend on the assumption that the inspired gas composition is consistent.

Embodiments of the present invention can have a number of advantages. For example, device embodiments can be simple, lightweight, inexpensive, physically small, and easy to use. They can be digitally controlled and provide variable gas compositions at variable flow rates. Further, they can be readily adapted to a variety of pulmonary and cardiac tests, including stress testing. Additionally, they can provide an extremely low resistance to patient inspiration, which can be important not only for test accuracy but also for patients with chronic lung conditions.

These and other advantages will be apparent from the disclosure of the invention(s) contained herein.

Disclosed embodiments can provide a method for performing a pulmonary test including, while a patient inspires through the testing device, injecting a test gas at a selected flowrate toward an open end of the testing device; measuring a flow rate of the inspired gas, which comprises the test gas; and measuring a concentration of a selected test gas component in the inspired gas.

The above-described embodiments and configurations are neither complete nor exhaustive. As will be appreciated, other embodiments of the invention are possible utilizing, alone or in combination, one or more of the features set forth above or described in detail below.

DETAILED DESCRIPTION

Figure 1:
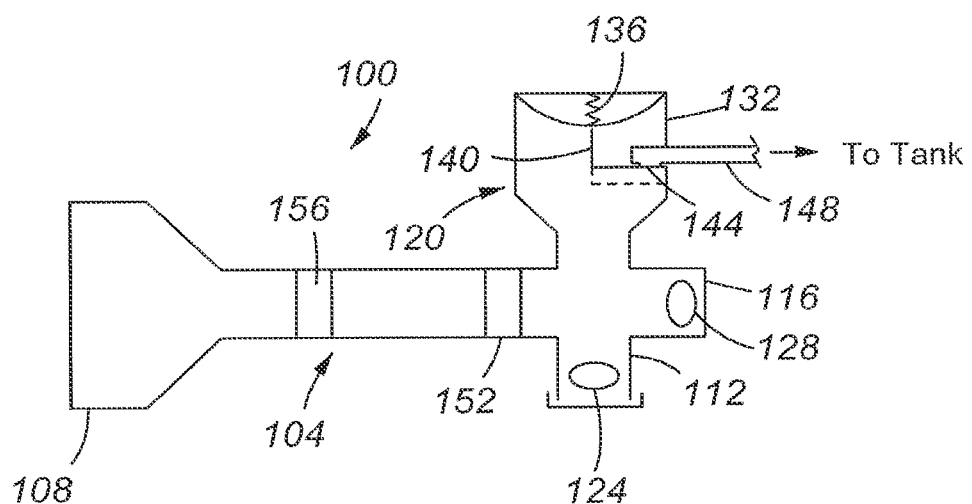
FIG. 1 is a cross-sectional view of a pulmonary testing device according to the prior art.
Figure 2B:
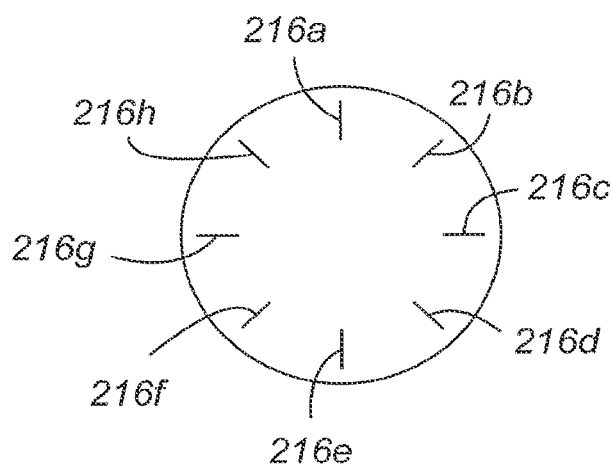
FIG. 2B is a cross-sectional view taken along line 2B-2B of FIG. 2A.
Figure 2A:
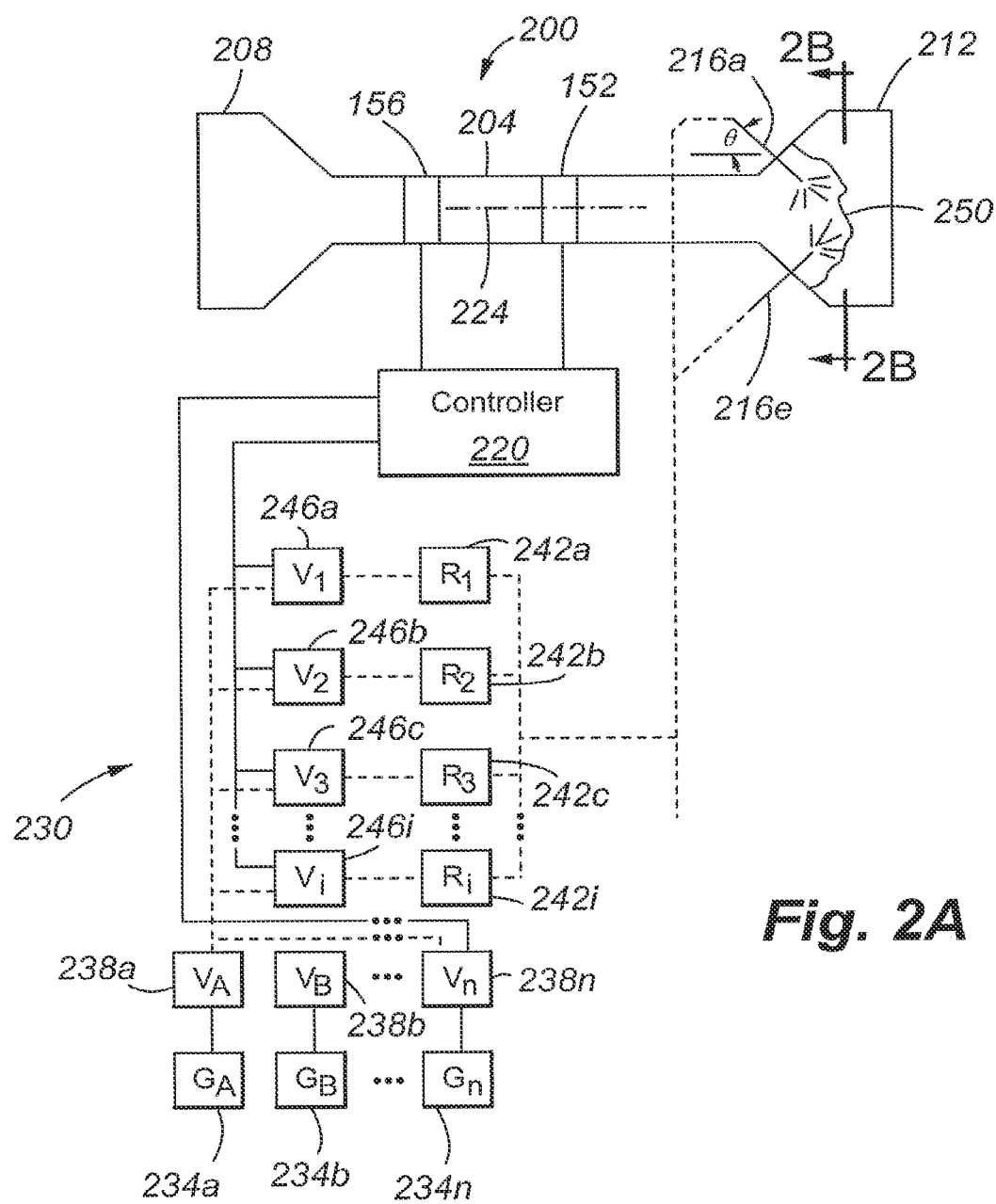
FIG. 2A is a cross-sectional view of a pulmonary testing device according to an embodiment of the present invention.

Referring to FIGS. 2A and 2B, a first embodiment of the pulmonary testing device 200 of the present invention will be discussed. The device includes a breathing conduit 204 having a patient mouthpiece 208 on one end and a test gas introduction inlet 212 on the other end. A plurality of injectors 216a-h are positioned in the test gas introduction inlet 212 to provide desired test gases into the inlet 212 from a pressurized gas source. Positioned between the two ends of the conduit 204 are gas flow measuring device 156 and a set of gas component sensors or gas analyzers denoted by block 152. A controller 220 receives measurement signals from the device 156 and sensors, uses the measurements to determine pulmonary (lung) parameters, such as diffusion, and lung capacity, and, based thereon, control test gas introduction or flow rates through the injectors 216a-h and controls the test gas composition provided to the injectors 216a-h, the injection of the test gas during inspiration, and the termination of test gas injection during expiration.

The breathing conduit 204 is open at either end and preferably provides little, if any, resistance to patient inhalation (which can be important for patients with chronic lung conditions). In other words when test gas is not being introduced through the injectors, the patient can breathe ambient air by placing his mouth over the mouthpiece 208 and inhaling, which will draw ambient air through the open inlet 212. It is also desirable for breathing conduit 204 to have a small volume (dead space) to minimize the amount of re-breathed gas. The conduit 204 can be of any composition but preferably is plastic.

The injectors 216a-h preferably have an outlet orifice that is smaller than the diameter of the body of the injectors 216a-h to introduce the test gas into the inlet 212 at a higher velocity than the flow velocity through the injector body. The injectors are preferably angled away from the patient to introduce gas in a direction of flow that is away from the patient. This injector orientation avoids forcing test gas into the patient's lungs, which would otherwise decrease the accuracy of the test, Preferably, the angle θ measured relative to the horizontal center line 224 of the conduit 204 is less than 90 degrees and more preferably ranges from about 10 to about 75 degrees. Although eight injectors 216a-h are depicted in FIG. 2B it rill be appreciated that any number or configuration of injectors may be used so long as the test gas wall 250 is maintained, Moreover though variable flow rate injectors are discussed herein, it is to be understood that fixed flow rate injectors may be used with the fixed flow rate being sufficient to maintain the test gas wall 250.

The gas flow measuring device 200 can be device capable of measuring gas flow, including without limitation a pneumatach, an ultrasonic emitter and receiver, a variable orifice, a transducer, and combinations thereof.

The gas sensors or analyzers 152 typically include a plurality of gas sensors for measuring each selected gas component. The sensors are preferably distributed substantially uniformly across the cross-section of the conduit passage to provide more accurate gas component measurements. Any suitable gas sensors can be employed.

The controller 220 can be any suitable processor, including a microprocessor, and typically includes a memory for storing measurements, computational control and derivation modules, and other information. Although a digital gas delivery system is depicted in FIG. 2, it is to be understood that the concepts of the present invention work equally well with an analog gas delivery system.

A test gas supply assembly 230 is controlled by the controller 220 and provides a test gas of a desired composition at a desired flow rate. For controlling composition, the assembly 230 includes a plurality of gas storage vessels 234a-n, each having a different gas composition ("G"), and a corresponding plurality of valves ("V") 238a-n controlling flow out of the vessels. For controlling flow rate, the assembly 230 includes a plurality of flow restrictors ("R") 242a-i of different orifice sizes and corresponding flow valves ("V") 246a-i for controlling gas flow through the corresponding flow restrictor 242. Dashed lines represent gas flow lines for transporting gas to the injectors 216 while solid lines represent signaling control lines for conveying digital commands from the controller 220 to the various valves 246a-i and 238a-n.

To illustrate the operation of the test gas supply assembly 230 assume that "X" represents a selected flow rate, that the flow rate through each of the flow restrictors is a product of X with a selected flow factor (e.g., weigh the orifices in a binary scheme, such as the flow rate through valve 242a being 8X, through valve 242b being 4X, through valve 242c being 2X, and through valve 242i being X, which would provide sixteen different flow rates adjustable by a four-bit binary code), and that each of the vessels 234a-n contains a different gas component (e.g., vessel 234a contains carbon monoxide or acetylene, vessel 234b helium or methane, and vessel 234n molecular oxygen). The controller 220 can deliver a gas comprising a mixture of carbon monoxide or acetylene on the one hand and helium or methane on the other at a selected flow rate by opening valves 238a and b and a selected one or combination of valves 246a-i. As will be appreciated, each vessel 234 can include a mixture of gas components or a single vessel containing a selected mixture of gas components can replace all of the vessels depending on the application. The configuration of FIG. 2 can provide a simple, controllable and versatile pulmonary testing device.

The operation of the pulmonary testing device 200 will now be described with reference to FIGS. 2A, and 3-5.

To initiate a test, the controller 220 introduces a test gas mixture through the injectors 216 at a flow rate that provides a test gas volume over a selected period of time that is greater than the volume of gas that the patient will likely inspire over the same time period. The uniform distribution of test gas across the cross-section of the conduit 204 effectively provides a "wall" 250 of test gas that blocks or inhibits the flow of ambient air through the conduit 200 and into the patient's lungs. The requisite gas flow rate through the injectors depends on the number of gas injectors employed.

Figure 5:
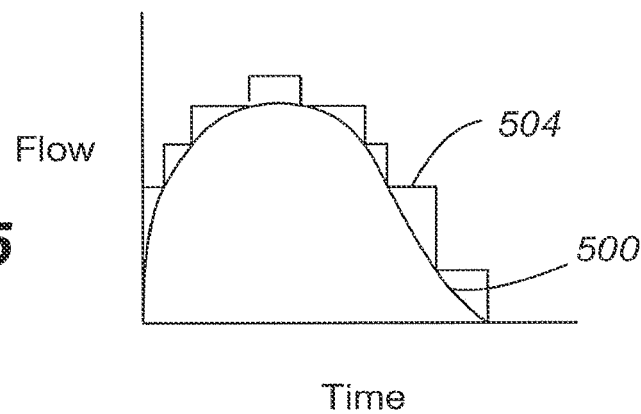
FIG. 5 is a plot of gas flow rate against time for an inspired gas flow.

The patient then commences inspiring the test gas through the mouthpiece 208. As the patient's inspiration rate (or the flow rate through the conduit 204) changes, the controller 220 issues commands to the valves 246a-i as required to simultaneously and equally decrease or increase the flow rates through the injectors to maintain a bulk introduction gas flow rate that is sufficient to compensate for the gas being inspired by the patient. With reference to FIG. 5 for example, the curve 504 represents the collective flow rate through injectors that, at any point in time, is effectively equal to the flow rate through the conduit as measured by the flow rate sensor 156. As can be seen from FIG. 5, the collective flow rate 504 through the injectors is maintained, over a selected time interval, at a magnitude that is greater than the flow rates on the curve 500 over the same interval.

In a preferred embodiment, during any selected time interval the flow rate through the injectors is maintained at a selected flow rate greater than the flow rates on the curve, where the selected flow rate is sufficient to maintain the test gas wall 250. In one embodiment, the controller 220 measures the current flow rate, determines the rate of change of the flow rate over a selected number of preceding time intervals, and, based on this information, predicts a likely flow rate over the subsequent time interval. The control signal sent to the valves 246a-i for valve control in the subsequent time interval is generally based on that prediction.

The inspired and/or expired gas component volumes can be determined using measurements from the flow and gas concentration sensors 156 and 152, respectively.

Figure 3:
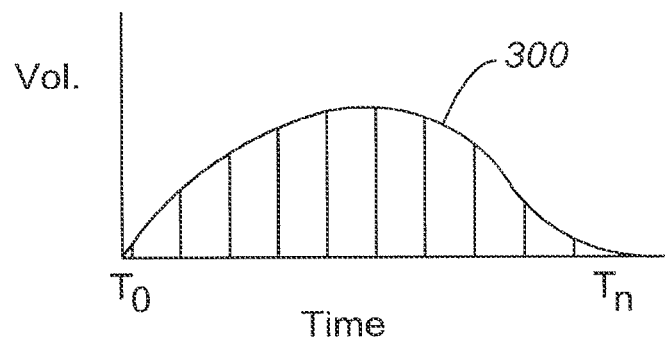
FIG. 3 is a plot of inspired gas volume (vertical axis) against time (horizontal axis) to provide a curve defining a series of gas flow rates.

FIG. 3 shows a typical patient inspiration curve 300 for a selected gas component X. The area under the curve represents the total volume of gas component X inspired by the patient over the time interval $T_0$ to $T_N$. The area may be determined using any known mathematical algorithms, such as integration. In a preferred embodiment, the area is determined using the following equation:

$$V_X = \sum \left[\frac{dV_1}{dt} F_X\right]_i \Delta T_i$$

where $V_X$ is the total volume of a selected gas component inspired by the patient, $$\frac{dV_1}{dt}$$

is the inspired flow rate over a sample interval (measured by the gas flow measuring device 156), $F_X$ is the fraction of the inspired gas flow during the sample interval that represents component X (measured by the gas sensors 152), and $\Delta T_i$ is the sample interval (which is usually the time interval between successive measurements), and i is the reference indicating which sample interval represents a member in a set of sample intervals. The various products are summed over the duration of the pulmonary test, which varies depending on the type of test being conducted.

Figure 4:
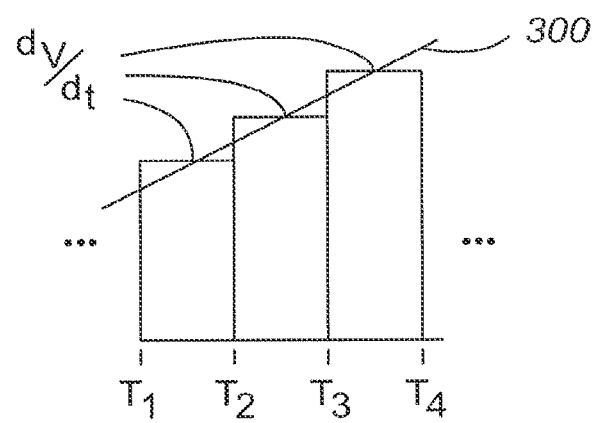
FIG. 4 is an enlarged view of a portion of the curve of FIG. 3.

The equation can be illustrated with reference to FIG. 4. FIG. 4 shows a series of sample time intervals, $T_1$-$T_2$, $T_2$-$T_3$, and $T_3$-$T_4$. The $$\frac{dV_1}{dt}$$

in each sample time interval is the average flow rate measured over each sample interval. As will be appreciated, $$\frac{dV_1}{dt}$$

can be determined in a number of ways, such as the median flow rate and the like. Using this equation, the dead space in the device 200 is substantially unimportant because of the accuracy of the algorithm in determining the volume of each component inspired into the lungs.

The gathered measurements can be used to perform a number of pulmonary tests. For example, the measurements can be used to determine lung volume, such as using gas wash-in methods (e.g., molecular nitrogen washout using molecular oxygen inspiration, methane single breath dilution, and multi-breath equilibration), (capillary and/or membrane) diffusion, such as using carbon monoxide or acetylene absorption coupled with a non-absorbable gas, and other lung mechanics and pulmonary function known to those of ordinary skill in the art. The device 200 is particularly useful in performing one or more of the foregoing tests while the patient is exercising. The device 200 can be lightweight, easily manipulated by the patient, and can provide (without using a new device 200) a varying inspired gas composition depending on the particular test desired.

A number of variations and modifications of the invention can be used. It would be possible to provide for some features of the invention without providing others.

For example in one alternative embodiment, a flow rate of sample gas is injected that is not sufficient to maintain a wall 250 of sample gas. In other words, ambient air is permitted to enter into the conduit 204 for inspiration by the patient while a sample gas is introduced through the injector(s). In this embodiment, the sample gas could be a single gas component or a mixture of gas components. The gas analyzers would permit the fraction of the inspired volume represented by a target gas component to be readily and accurately determined notwithstanding the presence of non-test gas components from the ambient atmosphere. This embodiment has the advantage of using a lesser volume of sample gas in the test, which can represent a significant cost savings. Patient safety can be ensured where a single component sample gas is used, such as a single component carbon monoxide or acetylene gas, by using a vessel 234 of a sufficient small volume that if the device 200 malfunctioned and introduced the entire volume of the vessel 234 into the conduit 204 the patient's health would not be compromised. Alternately, the concentration of the gas component can be limited to a safe maximum value such that it will not pose a health hazard even under prolonged breathing conditions.

Figure 6:
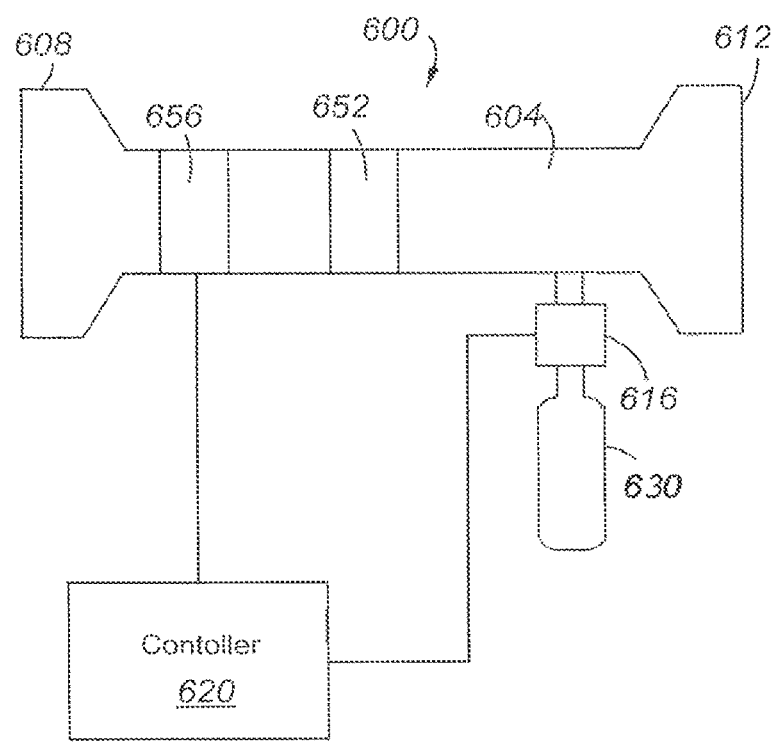
FIG. 6 is a cross-sectional view of a pulmonary testing device according to a second embodiment of the present invention.

An alternative embodiment in accordance with embodiments of the present invention is illustrated in FIG. 6. In the depicted embodiment, a small quantity of the test gas component(s) is stored in a small gas cartridge 630 at high concentrations (up to 100%). For example, a 2 ml gas cartridge storing 100% CO at 50 psi can provide over 1000 ppm of CO to a patient with an inspiratory capacity of 5 liters. The gas cartridge 630 is connected to the breathing conduit 604 through a valve mechanism. The valve mechanism can be an electrically actuated solenoid valve 616 or other suitable mechanisms. The valve 616 is actuated after the initiation of inspiring effort at an appropriate point during the test. The test gas stored in the gas cartridge 630 is discharged into the breathing conduit 604 to be inhaled by the patient. A restrictor in series with the valve 616 can also be employed to extend the gas discharge time to a few seconds to limit the peak concentration of gas component thereby reducing the dynamic range requirements for the gas sensors/analyzers 652. Similar to other embodiments, the flow sensor 656 and the gas sensors/analyzers 652 can be communicatively coupled to a controller 620 and/or can be operable to measure the total volume of test gas component inhaled. This embodiment has the advantage of eliminating the need for gas lines connecting the test gas source and the pulmonary test device. The small gas cartridge 630, preferably a single use item, can be easily stored and procured. The small size of the cartridge also ensures patient safety even if the entire content is discharged rapidly.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for performing a pulmonary test, comprising:
   while a patient inspires through a testing device such that the patient causes a stream of gas to flow from an open end of the testing device and through the testing device, injecting a test gas into the stream of gas via an injector directed towards the open end of the testing device, the injection of the test gas controlled by a processor, wherein, for a time interval, a volume of the test gas injected into the stream of gas is greater than a volume of gas inspired by the patient, and wherein the time interval comprises a plurality of successive sampling time intervals;
   measuring, using a gas flow sensor, a flow rate of the inspired gas, the inspired gas including at least a portion of the test gas;
   measuring a concentration of the test gas in the inspired gas; and
   injecting, for each sampling time interval from the plurality of successive sampling time intervals, a volumetric flow rate of the test gas that is greater than a volumetric flow rate of gas inspired by the patient.

2. The method of claim 1, wherein the injector is directed away from a patient mouthpiece of the testing device.

3. The method of claim 1, further comprising:
   changing a composition of the test gas while a mouthpiece of the testing device is in the patient's mouth.

4. The method of claim 1, further comprising:
   changing the volumetric flow rate of the test gas for each sampling time interval from the plurality of successive sampling time intervals.

5. The method of claim 1, further comprising:
   determining an inspired volume of the test gas using the following equation:

$$V_X = \sum \left[\frac{dV_1}{dt} F_X\right]_i \Delta T_i$$

where $V_X$ is a total volume of the test gas inspired by the patient, $$\frac{dV_1}{dt}$$

is a volumetric flow rate of the inspired gas over a sample interval, $F_X$ is a fraction of the test gas in the inspired gas during the sample interval, $\Delta T_i$ is the sample interval, and i is a reference indicating which member the sample interval represents in a set of sample intervals.

6. The method of claim 5, wherein the determining the inspired volume of the test gas is performed by the processor.

7. The method of claim 1, wherein the open end is open to ambient atmosphere while the patient inspires through the testing device.

8. The method of claim 1, wherein:
   the open end is open to ambient atmosphere while the patient inspires through the testing device; and
   the testing device includes a mouthpiece opposite the open end.

9. The method of claim 8, wherein:
   the testing device includes a breathing conduit fluidically coupling the open end to the mouthpiece; and the breathing conduit provides substantially no resistance to inspiration.

10. The method of claim 1, wherein:
the open end is open to ambient atmosphere while the patient inspires through the testing device;
the testing device includes a mouthpiece opposite the open end;
the testing device includes a breathing conduit fluidically coupling the open end to the mouthpiece; and
a volumetric flow rate at which the test gas is injected is greater than a volumetric flow rate of gas flowing through the mouthpiece, such that the test gas prevents or inhibits ambient atmosphere from being inspired.

11. The method of claim 10, wherein the volumetric flow rate at which the test gas is injected causes a uniform distribution of test gas across the breathing conduit that provides a wall of the test gas that prevents or inhibits the ambient atmosphere from being inspired.

12. The method of claim 1, wherein:
the open end is open to ambient atmosphere while the patient inspires through the testing device;
the testing device includes a mouthpiece opposite the open end;
the testing device includes a breathing conduit fluidically coupling the open end to the mouthpiece such that while the patient inspires, the stream of gas flows in a first direction from the open end, through the breathing conduit, and to the mouthpiece, the breathing conduit defining a centerline of the testing device; and
the injector is directed such that the test gas is injected along an injection direction that has an angle that is less than 90 degrees relative to the centerline.

13. The method of claim 1, wherein:
the open end is open to ambient atmosphere while the patient inspires through the testing device;
the testing device includes a mouthpiece opposite the open end; and
the testing device includes a breathing conduit fluidically coupling the open end to the mouthpiece, the breathing conduit defining a centerline of the testing device, the injector disposed at an angle that is less than 90 degrees relative to the centerline.

14. A method, comprising:
placing a mouthpiece of a testing device to a patient's mouth, the testing device having a first end portion containing the mouthpiece, a second end portion opposite the first end portion and containing an end open to ambient air, and a breathing conduit disposed between the first end portion and the second end portion;
measuring a volumetric flow rate of inspired gas flowing through the breathing conduit when the patient inspires, the inspired gas flowing from the end open to ambient air towards the mouthpiece; and
injecting a test gas into the inspired gas at the second end portion of the testing device while the inspired gas flows through the second end portion, the test gas injected via an injector directed towards the end open to ambient air, the injection of the test gas controlled by a processor, wherein the test gas is injected into the second end portion with a volumetric flow rate greater than the volumetric flow rate of the inspired gas such that the test gas prevents or inhibits ambient air from entering the breathing conduit when the patient inspires.

15. The method of claim 14, further comprising measuring a concentration of the test gas in the breathing conduit.

16. The method of claim 14, further comprising measuring a concentration of the test gas when the patient expires.

17. The method of claim 14, wherein a volumetric flow rate at which the test gas is injected causes a uniform distribution of test gas across the breathing conduit that provides a wall of the test gas that prevents or inhibits the ambient atmosphere from being inspired.

18. The method of claim 14, wherein the breathing conduit provides substantially no resistance to inspiration.

* * * * *